(12) United States Patent
Baird et al.

(10) Patent No.: US 8,728,515 B2
(45) Date of Patent: May 20, 2014

(54) ADJUVANTS FOR USE IN VACCINATION

(75) Inventors: Mark Stephen Baird, Gwynedd (GB); Juma' a Raheem Al-Dulayymi, Gwynedd (GB); Cornelia Theunissen, Gwynedd (GB); Gani Koza, Gwynedd (GB); Seppe Vander Beken, Ghent (BE); Johan Adriaan Marc Grooten, Ghent (BE)

(73) Assignees: Bangor University, Gwynedd (GB); Universiteit Gent, Ghent (BE)

( * ) Notice: Subject to any disclaimer, the term of this patent is extended or adjusted under 35 U.S.C. 154(b) by 641 days.

(21) Appl. No.: 12/988,587

(22) PCT Filed: Apr. 22, 2009

(86) PCT No.: PCT/GB2009/050410
§ 371 (c)(1),
(2), (4) Date: Mar. 4, 2011

(87) PCT Pub. No.: WO2009/130508
PCT Pub. Date: Oct. 29, 2009

(65) Prior Publication Data
US 2011/0142916 A1 Jun. 16, 2011

(30) Foreign Application Priority Data

Apr. 22, 2008 (GB) .................................. 0807306.6

(51) Int. Cl.
*A61K 9/127* (2006.01)
*A61K 39/00* (2006.01)
*C07C 61/00* (2006.01)
*C07D 303/12* (2006.01)

(52) U.S. Cl.
USPC ........ 424/450; 424/184.1; 549/561; 562/500; 562/506; 562/577; 562/579

(58) Field of Classification Search
USPC ........ 424/184.1, 450; 549/561; 562/500, 506, 562/577, 579
See application file for complete search history.

(56) References Cited

U.S. PATENT DOCUMENTS

2003/0175731 A1 9/2003 Fearon et al.
2007/0027098 A1 2/2007 Raz et al.

OTHER PUBLICATIONS

Parant M et al., Infection Immunity, vol. 20, No. 1, 1978.*

(Continued)

*Primary Examiner* — Deborah D Carr
(74) *Attorney, Agent, or Firm* — Norris McLaughlin & Marcus PA

(57) ABSTRACT

A compound of formula (I) for use as an adjuvant in vaccination; wherein R is an optionally-substituted alkyl, alkenyl, alkynyl, aryl, arylalkyl or alkylaryl moiety having from 1 to 50 carbon atoms; $R^1$ is an optionally-substituted alkyl, alkenyl, alkynyl, aryl, arylalkyl or alkylaryl moiety having from 1 to 40 carbon atoms; each of $R^2$, $R^3$ and $R^4$ is independently selected from an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkynylene, arylene, alkylarylene or cycloalkylene, ketone, ester, amide, imide, imine, thioether, ether, thioester, thioketone; and P is selected from hydrogen, an alkyl group, a sugar residue, or a metal, phosphonium or ammonium species; wherein at least one of X, Y and Z includes a moiety selected from cyclopropyl, C=A, C-AH and C—$OR^5$; wherein $R^5$ is alkyl or haloalkyl, and A is S, O or $NR^6$, wherein $R^6$ maybe H or 20 alkyl.

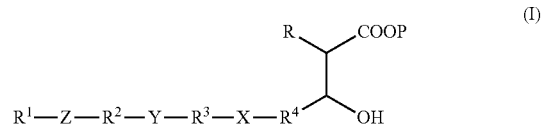

14 Claims, 4 Drawing Sheets

(56) References Cited

OTHER PUBLICATIONS

Figure 1:
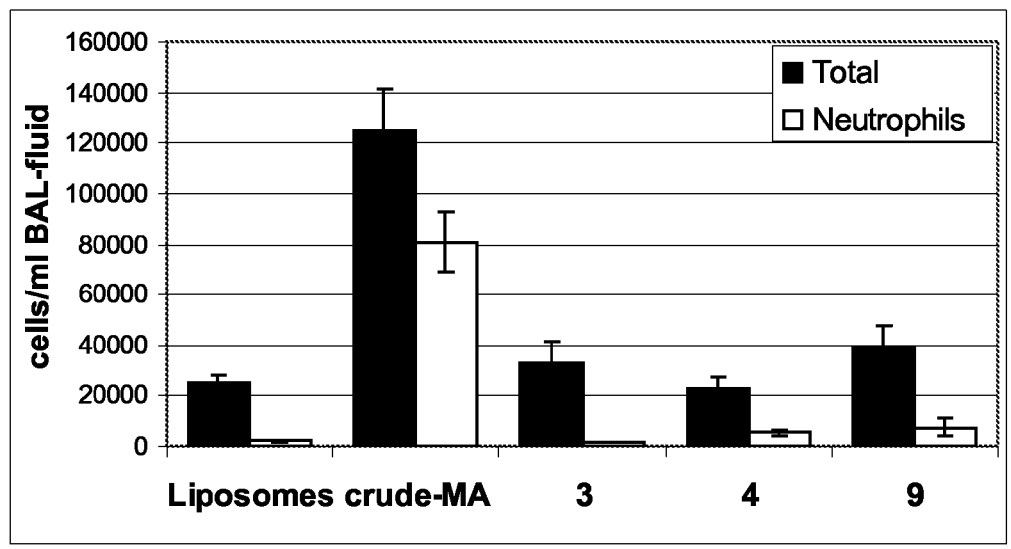

Asselineau J et al., Frontiers in Bioscience 1998, vol. , pp. 164-174.*
Al-Dulayymi J R et al., Tetrahedron, 2006, vol. 62, pp. 4851-4862.*
XP025383894, Al Dulayymi J R et al: "The Synthesis of a Single Enantiomer of a Major Appha-Mycolic Acid of M. Tuberculosis", Tetrahedron, Elseview Science Publishers, Amsterdam, NL, vol. 61, No. 50, pp. 11939-11951, Dec. 2005.
XP025001941, Al Dulayymi J R et al: The Synthesis of One Enantiomer of the Alpha-Methyl-Trans-Cycloprepane Unit of Mycolic Acids:, Tetrahedron, Elseview Science Publishers, Amsterdam, NL, vol. 62, No. 20, pp. 4851-4862, May 2006.
XP004173992, Coxon G D et al: "The Synthesis of Both Enantiomers of Lactobacillic Acid and Mycolic Acid Analogues", Tetrahedron Letters, Elsevier, Amsterdam, NL, vol. 40, No. 36, pp. 6689-6692, Sep. 1999.
XP002546342, Asselineau J et al: "Mycobacterial Lipids: A Historical Perspective", Frontiers in Bioscience: A Journal and Virtual Library, vol. 3, pp. 164-174, Oct. 1998.
XP002539259, Parant M et al., Nonspecific Immunostimulant Activities of Synthetic Trehalose-6, 6'-diesters (lower homologs of cord factor): Infection and Immunity, vol. 20, No. 1, Apr. 1978.
XP002539260, Bekierkunst A et al: "Immuno Therapy of Cancer with Nonliving BCG and Fractions Derived from Mycobacteria Role of Cord Factor Trealose 6 6 Di Mycolate in Tumor Regression" Infection and Immunity, vol. 10, No. 5, pp. 1044-1050, 1974.
XP022590789, Benadie Y et al: "Cholesteroid Nature of Free Mycolic Acids from M. Tuberculosis" Chemistry and Physics of Lipids, Limerick, IR, vol. 152, No. 2, pp. 95-103, Apr. 2008.
Temperature Dependence of the Langmuir Momolayer Packing of Mycolic Acids from Mycobacterium Tuberculosis M. Villeneuve et al, Biochimica et Biophysica Acta, (2005), 1715(2), 71-80.
The Specificity of Methyl Transferases Involved in Trans Mycolic Acid Biosynthesis in Mycobacterium Tuberculosis and Mycobacterium Smegmatis, B.G. Schroeder and C.E. Barry, Bioorganic Chemistry, (2001) 29, 164-177.
The Effect of Oxygenated Mycolic Acid Composition on Cell Wall Function and Macrophage Growth in Mycobacterium Tuberculosis Y. Yuan et al, Molecular Microbiology (1998), 29(6), 1449-1458.
"Synthetic Mirror Cord Factors: Proctected Dimycolyl Esters of an a, a -)1-1)-bisheptosiduronic acid" H.H. Baer and X. Wu, Carbohydrate Research, (1993), 245. 347-352.

\* cited by examiner

ADJUVANTS FOR USE IN VACCINATION

This is an application filed under 35 USC 371 of PCT/GB2009/050410.

The present invention relates to vaccines, and in particular to novel adjuvants for use therewith.

Vaccines have significantly contributed to human health during the last century by preventing many infectious diseases. Traditionally attenuated live or inactivated whole micro-organisms were injected. The use of such vaccines however harbours certain risks, especially in immune compromised individuals. The focus in the vaccination field has thus shifted towards the development of well-defined synthetic recombinant vaccines. Although much safer than the classical vaccines, these recombinant vaccines are also far less immunogenic than whole micro-organisms. Indeed, most protein antigens are not very immunogenic by themselves, and require the addition of immune stimulating agents called adjuvants to induce immune responses.

The only adjuvants as yet approved for human use in the US are Al(OH)$_3$ compounds. However whilst they are well suited for the induction of humoral immune responses, these adjuvants fail to induce cellular immunity. As a result they are largely ineffective against pathogens like viruses and intracellular bacteria for which protection against the body relies on cytotoxic T cells. There is thus an urgent need for adjuvants that can induce both arms of the immune response. The present inventors have now found that some classes of mycolic acid compounds may be useful as adjuvants in vaccination.

Mycolic acids are long chain fatty acid compounds typically having 60 to 90 carbon atoms and are found in the cell walls of mycobacteria. An example of such bacteria is *Mycobacterium tuberculosis*.

Two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in FIG. 1), can be differently substituted in both the proximal (the one nearer the hydroxy-acid) and the distal position (further from the carboxylic acid). The natural mycolic acids are broadly separated into classes, according to the groups present in the meromycolate moiety. The proximal or distal functional groups can be cyclopropanes, double bonds, an epoxy group, a methoxy group, carbonyl group, carboxyl group or methyl group. Details of the many different compounds that are found in natural sources of mycolic acid are given by M Watanabe, Y Aoyagi, H Mitome, T Fujita, H Naoki, M Ridell and D E Minnikin, *Microbiology* (2002), 148, 1881-1902; and M Watanabe, Y Aoyagi, Malin Ridell and D E Minnikin; *Microbiology* (2001), 147, 1825-1837.

Examples of the general structure of some sub-classes of mycolic acids are shown in FIG. 1:

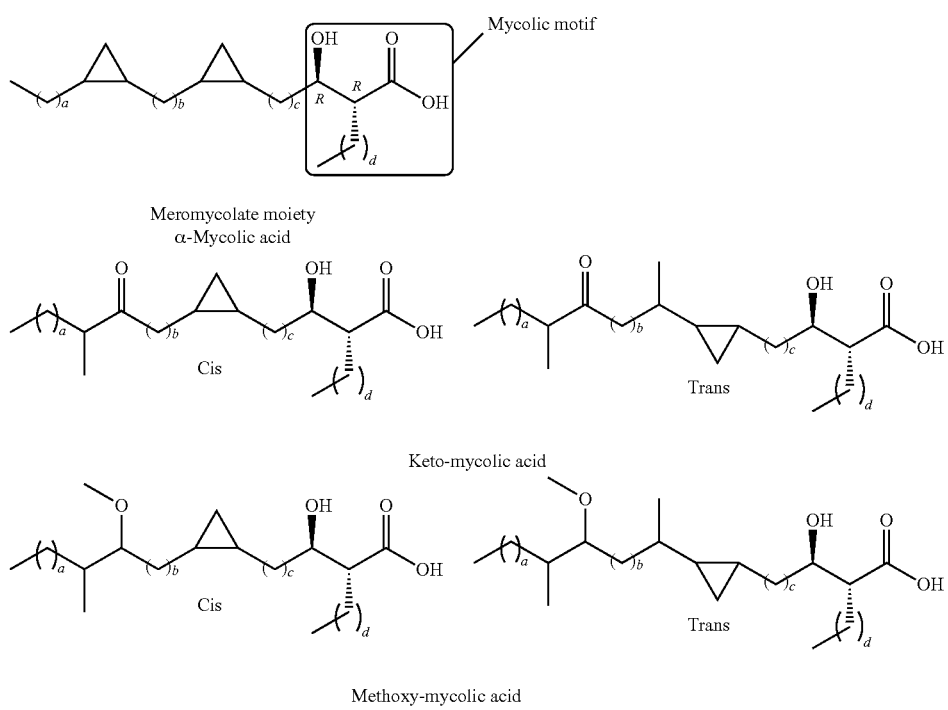

FIG. 1

Natural sources of mycolic acids, for example the cell walls of mycobacteria such as *Mycobacterium tuberculosis* include mixtures of different classes of compounds and different homologues. Separation of these compounds is a tedious undertaking and thus very little is known about the properties of the individual separated components. For example, most biological testing carried out previously has been done on mixtures extracted from natural sources of compounds.

The present inventors have prepared synthetic compounds as single stereoisomers of a number of mycolic acids which are identical or closely analogous to single compounds in the natural mixtures. They have surprisingly found that single compounds representative of certain sub-classes including particular functionalities have advantageous properties compared with other sub-classes or mixtures thereof.

In particular, compounds from certain subclasses may be particularly useful as adjuvants in vaccination.

According to a first aspect of the present invention there is provided a compound of formula I:

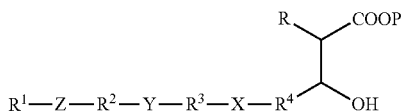

for use as an adjuvant in vaccination;
wherein R is an optionally-substituted alkyl, alkenyl, alkynyl, aryl, arylalkyl or alkylaryl moiety having from 1 to 50 carbon atoms; $R^1$ is an optionally-substituted alkyl, alkenyl, alkynyl, aryl, arylalkyl or alkylaryl moiety having from 1 to 40 carbon atoms; each of $R^2$, $R^3$ and $R^4$ is independently selected an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkynylene, arylene, alkylarylene or cycloalkylene, ketone, ester, amide, imide, imine, thioether, ether, thioester, thioketone; and P is selected from hydrogen, an alkyl group, a sugar residue, or a metal, phosphonium or ammonium species;
wherein at least one of X, Y and Z includes a moiety selected from cyclopropyl, C=A, C-AH and C—$OR^5$; wherein $R^5$ is alkyl or haloalkyl, and A is S, O or $NR^6$, wherein $R^6$ may be H or alkyl.

R is preferably an optionally-substituted alkyl, alkenyl, alkynyl, aryl or alkylaryl moiety having from 4 to 40 carbon atoms, preferably from 6 to 36 carbon atoms, for example from 10 to 32 carbon atoms, preferably from 16 to 30 carbon atoms, for example from 18 to 28 carbon atoms, preferably from 20 to 26 carbon atoms. Most preferably R has from 22 to 24 carbon atoms.

R may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably R is an optionally-substituted alkyl or alkenyl group. If R is an alkenyl group, it preferably includes at most one double bond for every six carbon atoms, more preferably at most one double bond for every ten carbon atoms. Any double bonds present may have an E or Z configuration. In preferred embodiments however R does not include any double bonds and is an alkyl group.

Preferably R is an optionally substituted alkyl or alkenyl moiety which includes no more than one substituent per four carbon atoms, preferably no more than one substituent for every six carbon atoms, preferably no more than one substituent for every ten carbon atoms, and most preferably no more than one substituent for each sixteen carbon atoms in the chain. Most preferably R is an unsubstituted alkyl group.

Most preferably R is an optionally-substituted alkyl or alkenyl chain. It may be straight chain or branched. Most preferably it is substantially straight chained and any branching is minimal, for example one or two methyl or ethyl residues may be branched from a long main chain. In especially preferred embodiments R is not branched.

Most preferably R is an unsubstituted alkyl chain having from 16 to 30 carbon atoms. In especially preferred embodiments R is an unsubstituted straight chain alkyl group having from 22 to 24 carbon atoms.

$R^1$ is an optionally-substituted alkyl, alkenyl, alkynyl, aryl or alkylaryl moiety having preferably from 4 to 36 carbon atoms, more preferably from 6 to 32 carbon atoms, for example from 8 to 28 carbon atoms, preferably from 10 to 24 carbon atoms, for example from 12 to 22 carbon atoms. Most preferably $R^1$ has from 16 to 20 carbon atoms.

$R^1$ may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably $R^1$ is an optionally-substituted alkyl or alkenyl group. If $R^1$ is an alkenyl group, it preferably includes at most one double bond for every six carbon atoms, more preferably at most one double bond for every ten carbon atoms. Any double bonds present may have an E or Z configuration. In preferred embodiment, $R^1$ does not contain any double bonds and is an alkyl group.

Preferably $R^1$ is an optionally substituted alkyl or alkenyl moiety which includes no more than one substituent per four carbon atoms, preferably no more than one substituent for every six carbon atoms, preferably no more than one substituent for every ten carbon atoms, and most preferably no more than one substituent for every twelve carbon atoms in the chain. Preferably $R^1$ is an unsubstituted alkyl chain.

Most preferably $R^1$ is an optionally-substituted alkyl or alkenyl chain. It may be straight chain or branched. Most preferably it is substantially straight chained and any branching is minimal, for example one or two methyl or ethyl residues may be branched from a long main chain. In especially preferred embodiments $R^1$ is not branched.

Most preferably $R^1$ is an unsubstituted alkyl chain having from 12 to 24 carbon atoms. In especially preferred embodiments R is an unsubstituted straight chain alkyl group having from 16 to 20 carbon atoms.

$R^4$ is preferably alkylene, alkenylene, alkynylene, arylene, arylalkylene or alkylarylene moiety having from 2 to 36 carbon atoms, preferably from 4 to 30 carbon atoms, for example from 8 to 26 carbon atoms, more preferably from 10 to 20 carbon atoms and most preferably from 12 to 18 carbon atoms.

$R^4$ may be straight chained or may include branching and may optionally include substituents. $R^4$ may be substituted with one or more groups selected from hydroxyl, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably $R^4$ is an optionally-substituted alkylene or alkenylene group. If $R^4$ is an alkenylene group, it preferably includes at most one double bond for every six carbon atoms, more preferably at most one double bond for every ten carbon atoms. Any double bonds present may have an E or Z configuration. In preferred embodiments R⁴ does not include any double bonds and is an alkyl chain.

Preferably R⁴ is an optionally substituted alkylene or alkenylene moiety which includes no more than one substituent per four carbon atoms, preferably no more than one substituent for every six carbon atoms, preferably no more than one substituent for every ten carbon atoms, more preferably no more than one substituent for each sixteen carbon atoms in the chain. Most preferably R⁴ is an unsubstituted alkylene chain.

R⁴ may be straight chained or may include some branching. In preferred embodiments, however, R⁴ is a straight chain alkylene residue having 12 to 18 carbon atoms.

Each of R² and R³ may be independently selected from an alkylene, alkenylene, alkynylene, arylene, arylalkylene and alkylarylene moiety having from 1 to 30 carbon atoms, preferably 4 to 20, more preferably from 6 to 15 carbon atoms.

Each of R² and R³ may be straight chained or may include branching and may optionally include substituents. Each may be independently substituted with one or more groups selected from hydroxyl, alkoxy (especially methoxy), halo (especially chloro or fluoro), nitro, sulfoxy, alkylsulfoxy, amino, mercapto and trifluoromethyl.

One or more hetero atoms may be incorporated into either or each chain, for example O, S or N to form an ether, a thioether or an amine. Either or each chain may be alkenyl and thus may include one or more double bonds.

Preferably each of R² and R³ is an optionally-substituted alkylene or alkenylene group. If either or each is an alkenylene group, it preferably includes at most one double bond for every six carbon atoms, more preferably at most one double bond for every ten carbon atoms. Any double bonds present may have an E or Z configuration. Preferably R² does not contain any double bonds. Preferably R³ does not contain any double bonds.

Preferably each of R² and R³ is an optionally substituted alkylene or alkenylene moiety which includes no more than one substituent per four carbon atoms, preferably no more than one substituent for every six carbon atoms, preferably no more than one substituent for every ten carbon atoms in the chain. Preferably R² is unsubstituted. Preferably R³ is unsubstituted.

Most preferably each of R² and R³ is an alkylene residue which is unsubstituted and straight chained.

P may be hydrogen to provide the free acid, or alkyl to provide an ester, a metal, ammonium or phosphonium species, or a sugar residue. Suitable sugar residues include arabinose, trehalose and glucose.

In some preferred embodiments, P is hydrogen.

Each of X, Y and Z may be independently selected from an alkylene group, a cycloalkylene group, a moiety including a ketone, a thioketone or an imine, a moiety including a hydroxyl, thiol or amine moiety, a moiety including an alkoxy or haloalkoxy residue, a moiety including an epoxide or a moiety including an alkene; with the proviso of course that at least one of X, Y and Z includes a moiety selected from cyclopropyl, C=A, C-AH and C—OR⁵.

Preferably at least one of X, Y and Z includes a moiety C=O or C—OR⁵. More preferably at least one of X, Y and Z includes a moiety C—OR⁵. Most preferably at least one of X, Y and Z includes a moiety C-OMe.

Suitably each of X, Y and Z contributes a two or three carbon fragment to the main alkyl chain i.e. the carbon backbone. Such a 2 or 3 carbon fragment may suitably include a methyl substituent.

Figure 2:
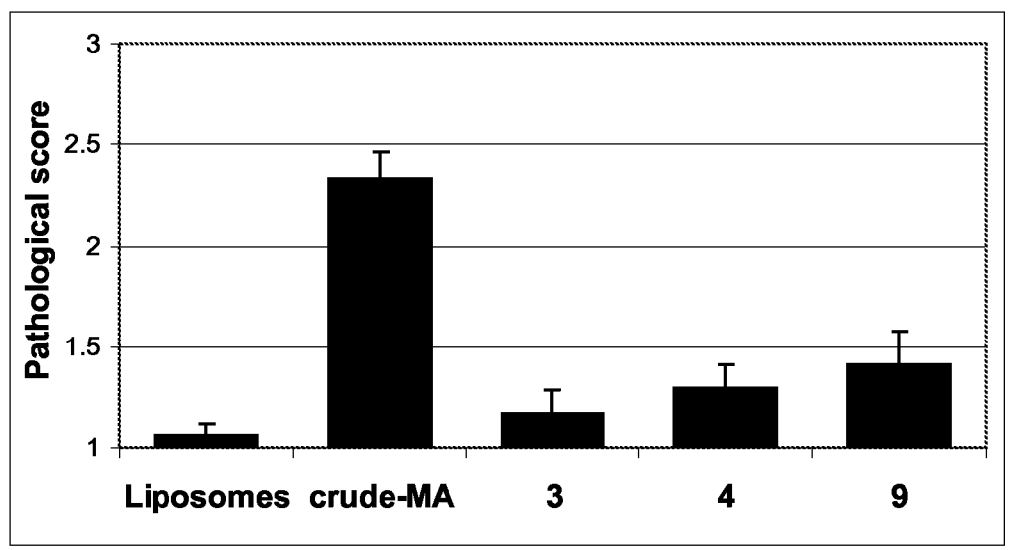

Preferably each of X, Y and Z is independently selected from one or more of the units shown in FIG. 2:

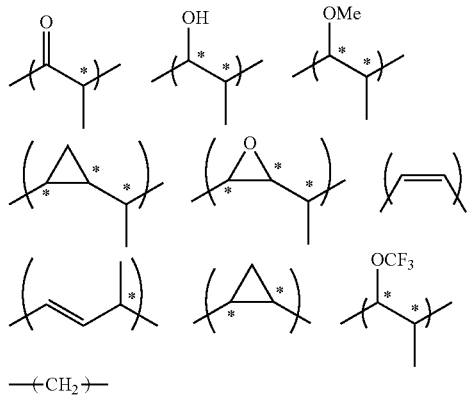

FIG. 2

The substituents may be included in either orientation with respect to the mycolic acid motif; hence either regioisomer may be present. Further the unit may include any of the possible stereoisomers resulting from the different chiral centres indicated (*) in FIG. 2.

In preferred embodiments Y is CH₂ and thus the unit "R²—Y—R³" may be regarded in preferred embodiments as an alkylene chain of formula (CH₂), in which n is preferably from 1 to 40, more preferably from 5 to 30, preferably from 10 to 25, for example from 16 to 22.

In preferred embodiments X includes a cyclopropyl moiety. This group may have a cis or a trans configuration. In some preferred embodiments it has trans configuration.

In some preferred embodiments X includes a methyl substituent. The carbon carrying the methyl substituent may have an (R) or (S) configuration.

In some embodiments X may contribute to the main chain a two-fragment unit including a cyclopropyl unit or a three-carbon unit including a cyclopropyl unit and on an adjacent carbon a methyl substituent. In such embodiments the methyl substituent may be between the cyclopropyl unit and the mycolic acid motif, that is proximal to the mycolic acid motif, or it may be distal from the mycolic acid motif. Preferably it is distal from the mycolic acid motif. Any relative stereochemistry between the cyclopropane moiety and methyl group may be present. Suitably the α-methyl cyclopropyl unit has (R), (S), (R) or especially (S), (R), (S) stereochemistry.

In some embodiments X includes an alkene. This may be a cis or trans alkene. It may be di- or trisubstituted. Preferably it is disubstituted. X may include a methyl substituent at a position α to the alkene moiety. Such a methyl substituent may be proximal or distal relative to the mycolic acid functionality.

In some embodiments X is a group of formula (CH₂), in which n maybe from 1 to 10, preferably 1 to 4.

In preferred embodiments the group Z includes a moiety selected from cyclopropyl, C=A, C-AH and C—OR⁵. More preferably Z includes either the moiety C=A or C—OR⁵. Most preferably Z includes the moiety C—OR⁵.

Thus in some preferred embodiments group Z includes a moiety C—OR⁵. The carbon atom lies in the main long chain of the molecule and carries the substituent R⁵O. R⁵ is alkyl or haloalkyl, preferably C₁ to C₄ alkyl or haloalkyl. In some preferred embodiments R⁵ is C₁ to C₄ alkyl and may suitably be methyl, ethyl, propyl (including isopropyl and n-propyl) or butyl (including n-butyl, tert-butyl, isobutyl and sec-butyl). Preferred are methyl and ethyl. Most preferably R⁵ is methyl i.e. Z is a group having a methoxy substituent.

In some embodiments $R^5$ may be $C_1$ to $C_4$ haloalkyl. A haloalkyl group includes any alkyl group in which one or more hydrogen atoms has been replaced by a halogen atom, for example bromine, chlorine or fluorine. Preferred haloalkoxy moieties are those including one or more chlorine or, especially fluorine atoms. Suitably all of the hydrogen atoms of an alkyl group have been replaced with halogen atoms in the haloalkoxy group, preferably all have been replaced with fluorine. Especially preferred haloalkoxy groups are pentafluoroethoxy, trifluoroethoxy and most preferably trifluoromethoxy.

The alkoxy or haloalkoxy group is suitably appended directly to a carbon atom that lies in the main long chain of the molecule.

In some preferred embodiments Z is a two-carbon fragment which includes an alkoxy or haloalkoxy (especially methoxy) substituent and α to this group a methyl substituent.

The methyl substituent may have any relative stereochemistry compared with the alkoxy or haloalkoxy group and each of the carbon atoms bearing the methyl group and the methoxy group may be (R) or (S) independently.

Thus in some preferred embodiments Z includes an α-methyl β-alkoxy moiety, or an α-methyl β-haloalkoxy moiety. An α-methyl β-alkoxy moiety is preferred and an α-methyl β-methoxy moiety is especially preferred.

The methyl group may be distal from the mycolic acid motif relative to the alkoxy or halo functionality or it may be proximal. Preferably the methyl is distal from the mycolic acid motif.

In some preferred embodiments, Z includes a group of formula C=A wherein A is O, S or $NR^6$.

$R^6$ may be hydrogen or an alkyl group. When $R^6$ is an alkyl group, it is preferably an alkyl group having 1 to 10 carbon atoms, more preferably from 1 to 4 carbon atoms, for example methyl or ethyl.

The carbon atom of the group C=A or C-AH lies in the main long chain of the molecule.

In some especially preferred A is O and the group Z includes a carbonyl functionality. The preferred carbonyl group is a ketone.

In some preferred embodiments Z is a two-carbon fragment which includes ketone and α to this group a methyl substituent.

When Z includes an α methyl ketone, the carbon atom carrying the methyl group may have either stererochemistry. However this is a readily epimerisable centre and thus a racemic mixture is commonly found.

In some especially preferred embodiments Z includes an α-methyl ketone.

The methyl group may be distal to the mycolic acid motif relative to the ketone/alcohol functionality or it may be proximal. Preferably the methyl is distal from the mycolic acid motif.

In some embodiments Z includes a cyclopropyl group. Suitably, two carbon atoms of the cyclopropyl group lie within the long carbon chain. The cyclopropyl group may have a cis or a trans configuration.

In some embodiments Z may contribute to the main chain a two-fragment unit including a cyclopropyl unit or a three-carbon unit including a cyclopropyl unit and on an adjacent carbon a methyl substituent. Such a methyl group may have an (R) or an (S) configuration. In such embodiments the methyl substituent may be proximal to the mycolic acid motif, or it may be distal from the mycolic acid motif. Preferably it is distal from the mycolic acid motif. Any relative stereochemistry between the cyclopropane moiety and methyl group may be present. Suitably the α-methyl cyclopropyl unit has (R), (S), (R) or especially (S), (R), (S) stereochemistry.

In especially preferred embodiments, the present invention provides compounds of formula IIa, IIb, IIc or IId:

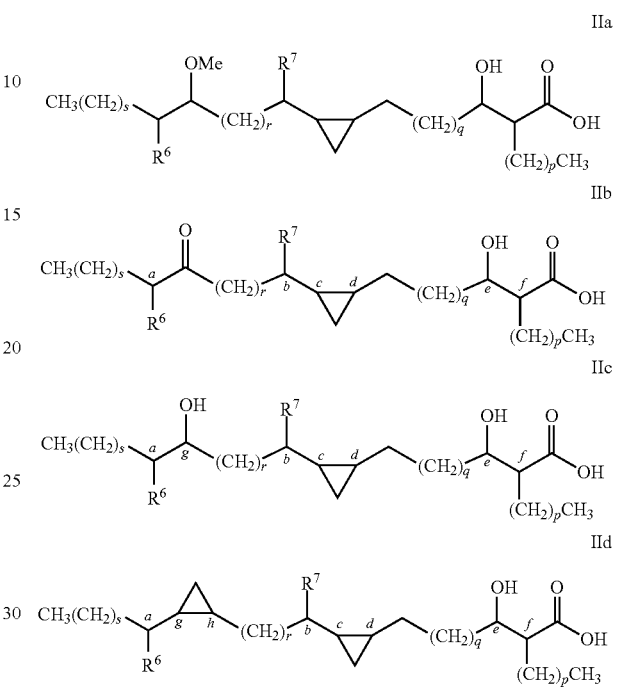

for use for use as an adjuvant in vaccination.

It should be noted that the compounds of formula IIa, IIb, IIc and IId are a subset of the compounds of formula I. Thus subsequently in this document when reference is made to compounds of formula I, this includes compounds of formula IIa, IIb, IIc or IId, as preferred embodiments.

In preferred embodiments the present invention provides compounds of formula IIa or IIb for use for use as an adjuvant in vaccination. In especially preferred embodiments the present invention provides compounds of formula IIa for use for use as an adjuvant in vaccination.

In each of the structures IIa, IIb, IIc and IId $R^6$ may be hydrogen or $C_1$ to $C_4$ alkyl. Preferably $R^6$ is methyl or hydrogen.

In each of the structures IIa, IIb, IIc and IId $R^7$ may be hydrogen or $C_1$ to $C_4$ alkyl. Preferably $R^7$ is methyl or hydrogen.

In structures IIa, IIb, IIc and IId, p is preferably from 4 to 40, preferably from 8 to 36, more preferably from 12 to 32, for example from 16 to 30, more preferably from 20 to 28, for example from 22 to 26.

In structures IIa, IIb, IIc and IId, q is preferably from 2 to 40, more preferably from 4 to 36, for example from 6 to 32, preferably from 8 to 28, for example from 10 to 24 and preferably from 14 to 20.

In structures IIa, IIb, IIc and IId, r is preferably from 2 to 40, for example from 4 to 36, preferably from 6 to 30, for example from 8 to 24, and preferably from 14 to 20.

In structures IIa, IIb, IIc and IId, s is preferably from 2 to 40, for example from 6 to 36, preferably from 10 to 32, for example from 12 to 28, and preferably from 14 to 24.

Any or all of the stereocentres indicated by a, b, c, d, e, f, g or h in structures IIa or IIb may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IIa it is possible that the stereocentre designated a will be racemic as this is a readily epimerisable position.

The stereocentre indicated at position a may have an (R) or an (S) configuration.

The stereocentre at b may have an (R) or an (S) configuration.

The stereocentre at c may have an (R) or an (S) configuration.

The stereocentre at d may have an (R) or an (S) configuration.

The stereocentre at e may have an (R) or an (S) configuration.

The stereocentre at f may have an (R) or an (S) configuration.

The stereocentre at g may have an (R) or an (S) configuration.

The stereocentre at h may have an (R) or an (S) configuration.

According to a second aspect of the present invention there is provided compounds of formula I except for compounds of formula III:

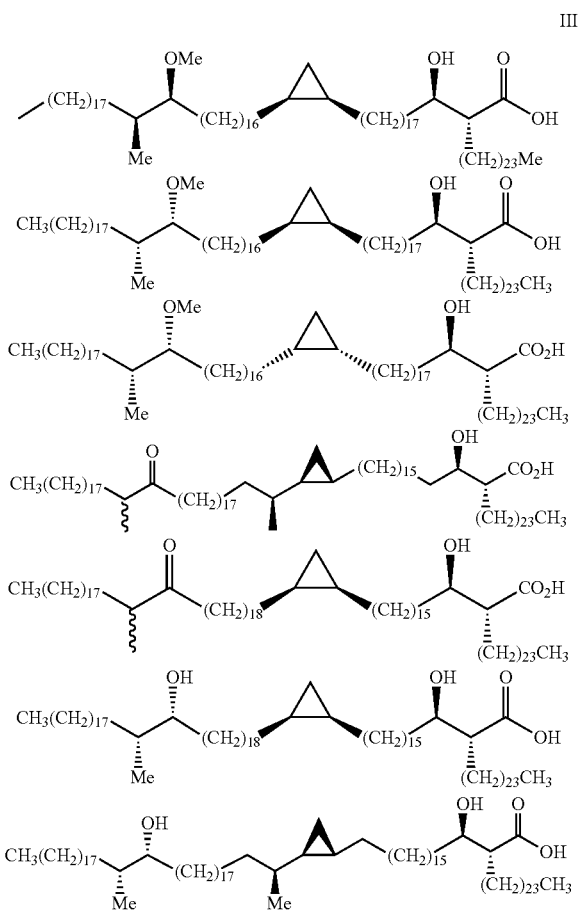

Compounds of formula I are as defined in relation to the first aspect and preferred features of the first aspect apply equally to the second aspect.

The compounds of the second aspect are suitably available in highly purified forms, preferably as single homologues and preferably single regioisomers and single stereoisomers. Suitable they are at least 90% pure, preferably at least 95% pure, for example at least 98% or 99% pure.

The compounds of the present invention may be prepared by any suitable means. They may be extracted from natural sources and purified. They may be prepared by biosynthetic methods or they may be prepared synthetically.

Preferably the compounds of the present invention are prepared synthetically. An advantage of using compounds which are prepared synthetically is that single compounds can be prepared in very high purity having a single stereochemistry. A disadvantage of compounds isolated from natural sources for example, is that mixtures are often obtained, including different isomers and/or different classes of mycolic acids and/or in particular different homologues. Although these other compounds may sometimes only be present in trace amounts, for pharmaceutical use synthetic compounds not containing other stereoisomers or homologues are highly desirable. It is possible that defined mixtures of synthetic compounds may be used in the present invention. However the exact composition of such mixtures may be carefully controlled to include known amounts of individual components which have been prepared separately and characterised.

Suitable methods for preparing compounds for use in the present invention are described in previous publications of the inventors. See for example Al Dulayymi J R, Baird M S and Roberts E, Chem Commun (Camb) 2003:228-9; Al Dulayymi J R, Baird M S and Roberts E., Tetrahedron 2005; 61:11939-11951; Al Dulayymi J R, Baird M S, Roberts E, Deysel M and Verschoor J., Tetrahedron 2007; 63:2571-2592; Al Dulayymi J R, Baird M S, Roberts E and Minnikin D E., Tetrahedron 2006; 62:11867-11880; Al-Dulayymi J R, Baird M S, Mohammed H, Roberts E and Clegg W., Tetrahedron 2006; 62:4851-4862; Koza G, Baird M S., Tetrahedron Letters 2007; 48:2165-2169; and Toschi G, Baird M S., Tetrahedron 2006; 62:3221-3227.

According to a third aspect of the present invention there is provided a composition comprising a mixture of two or more compounds of formula I.

Such mixtures may include in addition to quite structurally different compounds and homologues, mixtures of different stereo and/or regio-isomers. However an advantage of such mixtures of the present invention is that controlled mixtures including specific amounts of well defined components can be prepared whereas natural mixtures may contain unknown or variable amounts of the various components and may include unidentified components.

According to a fourth aspect of the present invention there is provided a vaccine composition comprising a compound of formula I and an antigen.

It is believed that particular compounds of formula I may be selected to control the immune response achieved in vaccination. For example some compounds may be particularly effective adjuvants for use in vaccination against extracellular antigens, for example viruses and extracellular bacteria. Such compounds may then preferentially elicit Th17 and Th1 lymphocyte responses and immune defences supported by these T-cell subsets. Other compounds may be particularly effective adjuvants for use in vaccination against intracellular antigens, for example mycobacteria, *listeria* and cancer. Such compounds may then preferentially elicit Th1 and cytotoxic T-lymphocyte responses and immune defences supported by these T-cell subsets.

In some alternative embodiments the compound of formula I may be selected such that when used as an adjuvant a humoral immune response is elicited that is supported by Th2 lymphocytes and provides protection against among other parasitic infections.

The vaccine composition of the fourth aspect may include a single compound of formula I or it may include a mixture of two or more compounds of formula I, IIa, IIb, IIc and IId as defined in relation to the third aspect. The present invention relates to the use of compounds of formula I and especially those of formulae IIa, IIb, IIc and IId as an adjuvant in a vaccine. Preferably the compounds are used as an adjuvant for vaccines aimed at raising cellular immune responses where the level of immune protection raised will benefit from a cellular immune defence component.

Non-limiting examples of diseases in which raising of the cellular immune defence is desired include tuberculosis and other diseases caused by mycobacteria, pneumonitis induced by respiratory syncytial virus, cancer, malaria, and other diseases caused by bacterial, viral, fungal and parasitic infectious agents.

In some alternative embodiments the compound of formula I may be selected such that when used as an adjuvant a humoral immune response is elicited.

The compounds of the present invention may be used as an adjuvant in a vaccine for human use or in a vaccine for use on other mammals. It may be used in a vaccine for use on other animals, for example birds, fish, amphibians and reptiles.

The present invention may provide an adjuvant useful for the vaccination of livestock against diseases against which a cellular immune defence is required. Examples include bovine tuberculosis, avian flu and blue tongue.

The present invention may be also useful in providing an adjuvant for use in the vaccination of domestic or wild animals.

Any antigen may be used. The antigen may be provided in any suitable form, such as will be well understood by the person skilled in the art. For example it may be the pathogen inactivated by heat or fixated with formaldehyde, or a protein thereof or a peptide part of the protein combined or not with a hapten carrier, or a fusion protein of an antigenic protein or peptide and a carrier protein, or non-protein antigenic structures.

Preferably the vaccine composition further comprises a carrier. Any pharmaceutically acceptable carrier may be used.

The pharmaceutically-acceptable carrier may be a solid, for example polymer dust or a sugar; a micelle, for example a liposome; a liquid, for example a water-in-oil emulsion, or a solution, typically a saline solution or phosphate buffered saline; a gas; or a transdermal delivery system. When the carrier is a liquid, the composition may be in the form of a suspension or a vaporised liquid, typically a nebulisable physiological saline solution.

Preferred carriers are liposomes. Liposomes are phospholipid bilayers and are commonly used to deliver drugs to a target. Methods of formulating vaccine compositions using liposomes are well-known to those skilled in the art.

In some embodiments the antigen may be encapsulated within a microcapsule or other particulate carriers well-known to those skilled in the art and compounds of formula I may be carried on the surface of the microparticle.

Preferably the composition includes a carrier which is compatible with hydrophobic compounds as the adjuvant compounds of formula I are generally of a hydrophobic nature.

However many antigens are hydrophilic in nature and the vaccine composition must carry these. The vaccine composition may therefore comprise an emulsion or a carrier able to accommodate both hydrophobic and hydrophilic molecules. A liposome is an example of such a carrier: the mycolic acid adjuvant compound may be suitably absorbed into the hydrophobic region of the phospholipid wall while the antigen may be held within the liposome in a hydrophilic pocket.

The composition may comprise an oil-in-water emulsion or water-in-oil emulsion in which the adjuvant is dissolved in the oleophilic phase and the antigen is dissolved in the aqueous phase.

The vaccine composition is preferably a liquid composition suitable for intramuscular injection. It may further comprise saline solution or phosphate buffered saline. It suitably comprises such a solution having dispersed therein liposomes carrying an antigen and the mycolic acid derived adjuvant compound(s).

In some embodiments the vaccine composition may include two or more compounds of formula I. Selection of an appropriate mixture may allow manipulation of the immune response elicited to include additional types of immune defences.

The vaccine composition of the fourth aspect may further comprise one or more optional excipients, for example fillers, antioxidants and stabilisers.

In some embodiments the formulation which is suitable for direct administration to a patient may not be stable to storage. The present invention may thus provide a kit comprising precursor compositions which should be mixed immediately prior to administration. Such precursor compositions may typically include a first composition comprising an antigen and a second composition comprising a compound of formula I. The kit may for example comprise dry carrier powder having absorbed thereon adjuvant compounds of formula I and an aqueous solution in which the antigen is dissolved or dispersed.

The form of the composition of the fourth aspect of the present invention will depend on the method by which it is intended to be administered. The composition of the fourth aspect may be formulated to enable it to be administered in any suitable form. For example, the compounds of the present invention could be administered via inhalation, intravenously, orally, subcutaneously, by intramuscular injection, by suppository or enema form, intranasally by topical application, buccally, sublingually or transdermally.

Suitably the composition is formulated for ease of administration by intramuscular injection.

Preferably the composition is such that it can be administered by a non-invasive method, for example intradermally by high-pressure vaccination guns.

According to a fifth aspect of the present invention there is provided a method of vaccinating a mammal against a disease, the method comprising administering to said mammal a compound of formula I and an antigen.

The compound of formula I and the antigen may be administered separately. In such embodiments, it is preferred that the compound of formula I is administered first followed by the antigen within a period of 0.1 to 24 hours, preferably within a period of 0.1 to 12, and especially within 0.1 to 6 hours.

However in preferred embodiments the method of the fifth aspect comprises administering to a mammal a single composition comprising compound of formula I and an antigen, i.e. the antigen and adjuvant are coadministered in the form of a composition of the fourth aspect.

Preferred features of the fifth aspect are as defined in relation to the first, second, third and fourth aspects.

Without wishing to be bound by any theory, it is believed that the uptake of compounds of formula I by local phagocytes such as tissue macrophages and dendritic cells induces them to become immunogenic antigen presenting cells that selectively steer naïve, antigen-specific CD4+ T-lymphocytes towards developing into Th1 and Th17 effector lymphocytes that are known to promote cellular immune defences. In addition, by promoting antigen cross-presentation to CD8+ T-lymphocytes, the generation of cytotoxic Tc effector lymphocytes is promoted, thus further enhancing cellular immune defences against among others viral and bacterial pathogens.

The present invention will now be further described with reference to the following non-limiting examples.

EXAMPLES

Animals for Experiments

Female C57BL/6J mice were purchased from Janvier and housed under specific pathogen free conditions in individually ventilated cages and fed ad libitum. Mice were 8-12 weeks old at the start of experiments.

Example 1

Comparative Samples

Natural mycolic acids were included as comparative samples. A crude mycolic acid isolate from *Mycobacterium tuberculosis* (H37Rv) was obtained from Sigma and is referred to in these examples as crude-MA.

Example 2

Synthesis of Model Mycolic Acid

A model synthetic compound containing the mycolic acid motif as a mixture of stereoisomers and a meromycolic chain free of functional moieties served as a control mycolate. It was obtained by condensation of two methyl behenate molecules with sodium methoxide, followed by reduction of the derived methyl ester of the corresponding keto-acid and ester hydrolysis. This comparative example is referred to as compound 1 and the structure thereof is shown in table 1.

Example 3

Preparation of Single Isomer of Keto-Mycolic Acid of Formula

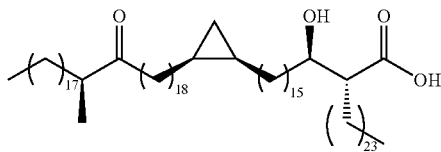

The compound having the structure above was prepared according to the following procedure. After each stage the structure of the product was fully characterised by NMR spectroscopy, IR, mass spectroscopy and the optical rotation was recorded.

Example 3a (8S,9S)-9-methyl-1-(tetrahydropyran-2-yloxy)-heptacosan-8-ol was prepared according to the method published by J. R. Al Dulayymi, M. S. Baird, E. Roberts, M. Deysel and J. Verschoor; Tetrahedron 63 (2007); 2571-2592. This material was protected as the tert-butyl dimethyl silyl ether by treatment with tert-butyl-dimethylsilylchloride and imidazole in DMF at room temperature. The product was then treated with Pyridinium-p-toluenesulfonate to give (8S,9S)-8-(tert-butyldimethylsilanyloxy)-9-methylheptacosane-1-ol. in (94% yield). The alcohol was oxidised using PCC to give (8S,9S)-8-(tert-butyldimethylsilanyloxy)-9-methylheptacosanal in 97% yield.

Example 3b 2,2-dimethyl-propionic acid 10-bromodecyl ester was prepared in 85% yield by treatment of 10-bromodecane-1-ol with trimethylacetyl chloride in the presence of pyridine and 4-dimethylaminopyridine at room temperature in dithlcromethane. After 18 hrs, the reaction was quenched by the addition of dilute hydrochloric acid worked up and filtered through silica to provide 2,2-dimethyl-propionic acid 10-bromodecyl ester.

The ester was treated with 1-Phenyl-1H-tetrazole-5-thiol and two equivalents of anhydrous potassium carbonate in acetone at room temperature for 18 hrs. Chromatography provided 2,2-dimethylpropionic acid 10-(1-phenyl-1H-tetrazol-5-ylsulfan-yl)decyl ester in 93% yield.

This compound was reacted with a solution of ammonium molybdate (VI) tetrahydrate in 35% $H_2O_2$ to provide 2,2-dimethylpropionic acid 10-(1-phenyl-1H-tetrazole-5-sulfonyl)decyl ester in 97% yield.

Example 3c

A THF solution comprising the compound prepared in example 3a and the compound prepared in example 3b was cooled to −10° C. and treated with lithium bis(trimethylsilyl) amide. After stirring at room temperature for 1.5 hrs the reaction worked up to provide 2,2-dimethylpropionic acid (E/Z)-(18S,19 S)-18-(tert-butyldimethylsilanyloxy)-19-methylhepta-triacont-10-enyl ester as a mixture of two isomers. These were reduced by hydrogenation using 10% palladium on carbon as a catalyst in ethanol and ethyl acetate.

The resultant ester was reduced using lithium aluminium hydride to provide (18S,19S)-18-(tert-butyldimethylsilanyloxy)-19-methylhepta-triacontan-1-ol as a colourless oil in 95% yield. The alcohol was then oxidised using PCC to give (18S,19S)-18-(tert-butyldimethylsilanyloxy)-19-methylheptatriacontanal in 95% yield.

Example 3d

The aldehyde obtained in example 3c was added to a stirred solution of butyric acid (1R,2S)-2-(1-phenyl-1H-tetrazole-5-sulfonylmethyl)-cyclopropylmethyl ester and treated with lithium bis(trimethylsilyl) amide at −5° C. Stirring at room temperature for 1% hrs and workup provided butyric acid (1R,2S)-2-[(E/Z)-(19S,20S)-19-(tert-butyldimethylsilanyloxy)-20-methyloctatriacont-1-enyl]-cyclopropyl methyl ester as a mixture of two isomers in a ratio of 2.5:1. This was reacted with 2,4,6-tri-isopropylbenzenesulphonyl hydrazide THF at 40° C. for 27 hrs. The reaction mixture was worked up and purified as above to give, butyric acid (1R,2S)-2-[(19S, 20S)-19-(tert-butyl-dimethyl-silanyloxy)-20-methyl-octatriacontyl]cyclopropyl methyl ester in 76% yield. This compound was reduced to the alcohol using lithium aluminium hydride and then oxidised with PCC to give (1R,2S)-2-[(19S, 20S)-19-(tert-butyldimethyl-silanyloxy)-20-methyloctatriacontyl]cyclopropanecarbaldehyde in 96% yield.

Example 3e

Acetic acid (R)-1-(2-benzyloxyethyl)-but-3-enyl ester was prepared from (S)-1-benzyl-oxyhex-5-en-3-ol by treatment with acetic anhydride and pyridine in toluene. This ester was treated with oxone and then $OsO_4$ to give (R)-3-acetoxy-5-benzyloxypentanoic acid in 78% yield. The acid was then refluxed in methanol under acidic conditions to provide the methyl ester Following deprotonation with lithium diisopropylamide, the methyl ester was treated with allyl iodide in the presence of HMPA. The product was purified by chromatography to provide (R)-2-((R)-3-benzyloxy-1-hydroxypropyl)pent-4-enoic acid methyl ester in 76% yield.

Example 3f

The compound obtained in example 3e was protected as the tert-butyl dimethyl silyl ether by treatment with tert-butyldimethylchlorosilane and imidazole in DMF. This compound was treated with 2,6-lutidine and $OsO_4$ 2.5% in 2-methyl-2-propanol, followed by $NaIO_4$ in 1,4-dioxane—water (3:1) at room temperature. The reaction was stirred at 25° C. for 2 hrs, quenched, and the product purified by chromatography to provide (2R,3R)-5-benzyloxy-3-(tert-butyldimethylsilanyloxy)-2-(2-oxoethyl)pentanoic acid methyl ester in 88% yield.

Example 3g

Lithium bis(trimethylsilyl)amide was added to a stirred solution of the compound formed in example 3f and 5-(docosane-1-sulfonyl)-1-phenyl-1H-tetrazole in THF. After stirring at room temperature for 3 hrs, the reaction was quenched and worked up to give (E/Z)-(R)-2-[(R)-3-benzyloxy-1-(tert-butyl-dimethylsilanyloxy)-propyl]-hexacosa-4-enoic acid methyl ester (6.43 g, 83%) as a mixture of two isomers in ratio 2:1. Hydrogenation in the presence of palladium 10% on in THF/IMS afforded (R)-2-[(R)-3-benzyloxy-1-(tert-butyldimethylsilanyloxy) propyl]hexacosanoic acid methyl ester in 98% yield.

Hydrogenation for 3 days in the presence of palladium 10% on carbon in ethyl acetate effected deprotection of the benzyl group in 95% yield. The resultant alcohol was then oxidised using PCC to provide (R)-2-[(R)-1-(tert-butyldimethylsilanyloxy)-3-oxopropyl]hexacosanoic acid methyl ester in 90% yield.

Example 3h

1-Phenyl-1H-tetrazole-5-thiol, 12-bromododecan-1-ol and anhydrous potassium carbonate were mixed together in acetone for 18 hrs at room temperature to provide 12-(1-phenyl-1H-tetrazol-5-ylsulfanyl)-dodecan-1-ol in 77% yield following work up and recrystallisation. Ammonium molybdate (VI) tetrahydrate in 35% $H_2O_2$ were added to a stirred solution of the solid in THF IMS (500 ml) at 10° C. and stirred at room temperature for 20 hrs. Work-up and crystallisation gave a white solid (m.p.: 56-58° C.), 12-(1-phenyl-1H-tetrazol-5-sulfonyl)-dodecan-1-ol in 95% yield. N-Bromosuccinimide was added to a solution of the alcohol and triphenylphosphine in dichloromethane and the reaction stirred at room temperature for 75 min. Work-up and purification by chromatography provided a white solid (m.p.: 63-65° C.), 5-(12-bromo-dodecane-1-sulfonyl)-1-phenyl-1H-tetrazole in 72% yield.

Example 3i

Lithium bis(trimethylsilyl)amide was added to a stirred THF solution of the compound prepared in example 3g and the compound prepared in example 3h. The reaction was stirred at room temperature for 3 hrs, quenched and purified by chromatography to provide (R)-2-[(E/Z)-(R)-15-bromo-1-(tert-butyldimethylsilanyloxy)penta-dec-3-enyl]hexacosanoic acid methyl ester (4.19 g, 82%) as a 2:1 mixture of two isomers. Hydrogenation in the presence of palladium 10% on carbon in THF and ethanol (1:1) gave (R)-2-[(R)-15-bromo-1-(tert-butyldimethylsilanyloxy)pentadec-yl]hexacosanoic acid methyl ester in 92% yield after 3 hours.

Example 3j

The compound prepared according to example 3i was stirred with 1-phenyl-1H-tetrazole-5-thiol and anhydrous potassium carbonate in acetone for 18 hrs at room temperature. Work-up and chromatography gave (R)-2-[(R)-1-(tert-butyldimethylsilanyloxy)-15-(5-phenyl-5H-tetrazol-1-ylsulfanyl)pentadecyl]hexacosanoic acid methyl ester in 86% yield.

The tert-butyldimethylsilyl protecting group was removed by stirring with HF and pyridine in THF in 84% yield and the resultant alcohol was reprotected as the acetate by treatment with acetic anhydride and anhydrous pyridine to give (R)-2-[(R)-1-acetoxy-15-(5-phenyl-5H-tetrazol-1-yl-sulfanyl)pentadecyl]hexacosanoic acid methyl ester in 83% yield.

This compound was treated with m-Chloroperbenzoic acid and $NaHCO_3$ in dichloromethane (40 ml) and stirred at room temperature for 20 hrs. Work-up and chromatography afforded a white solid, (R)-2-[(R)-1-acetoxy-15-(5-phenyl-5H-tetrazol-1-sulfonyl)pentadecyl]hexacosanoic acid methyl ester in 82% yield.

Example 3k

The ester obtained in example 3j was dissolved in dry THF along with (1R,2S)-2-[(19S,20S)-19-(tert-butyldimethylsilanyloxy)-20-methyloctatriacontyl]cyclopropane carbaldehyde and lithium bis(trimethylsilyl) amide was added. The solution was stirred at room temperature for 2 hrs, before being worked up and purified by chromatography to give (R)-2-((R)-1-acetoxy-16-{(1R,2S)-2-[(19S,20S)-19-(tert-butyldi-methylsilanyloxy)-20-methyl-octatriacontyl]cyclopropyl}hexadec-15-enyl)hexacosanoic acid methyl ester in 72% yield as a 4:1 mixture of two isomers.

Dipotassium azodicarboxylate was added to a stirred solution of the alkenes in THF and methanol (5:1) at 5° C. A solution of glacial acetic acid) and THF (2 ml) was added and the mixture was stirred for 48 hours. Work up and chromatography provided (R)-2-((R)-1-acetoxy-18-{(1R,2S)-2-[(19S,20S)-19-(tert-butyldimethyl-silanyloxy)-20-methyloctatriacontyl]cyclo propyl}octadecyl)-hexacosanoic acid methyl ester in 91% yield.

Example 3l

Removal of the tert-butyldimethylsilyl protecting group from the compound obtained in example 3k was achieved by treatment with HF and pyridine to provide (R)-2-((R)-1-acetoxy-16-{(1R,2S)-2-[(19S,20S)-19-hydroxy-20-methyloctatriacontyl]cyclopropyl}-octadecyl) hexacosanoic acid methyl ester in 73% yield after chromatography.

Treatment of the resultant alcohol with pyridinium p-toluene sulphonate and dihydro-2H-pyran added a THP protecting group 86% yield.

Hydrolysis of the ester was achieved by addition of lithium hydroxide monohydrate to a stirred solution of the ester in THF, methanol and water at room temperature. The mixture was stirred at 45° C. for 16 hrs, worked up and purified by chromatography to give (R)-2-((R)-1-hydroxy-16-{(1R,2S)-2-[(19S,20S)-20-methyl-19-(tetrahydropyran-2-yloxy)octatriacontyl]cyclopropyl}hexadecyl)hexacosanoic acid as a mixture of diastereoisomers in 60% yield.

Example 3m

The compound prepared in example 3l was protected as the tert-butyl-dimethylsilyl ester by treatment with tert-butyl-dimethylsilyl chloride and 4-dimethylaminopyridine. The product was purified by chromatography to give (R)-2-(R)-1-(tert-butyldimethylsilanyloxy)-16-{(1R,2S)-2-[(19S,20S)-20-methyl-19-(tetrahydropyran-2-yloxy)octatria-contyl]-cyclopropyl}hexa decyl)hexacosanoic acid as a mixture of diastereoisomers in 76% yield.

(Pyridinium-p-toluenesulfonate (100 mg, 0.40 mmol) was added to the above acid (100 mg, 0.07 mmol) in THF (4 ml), MeOH (0.5 ml) and $H_2O$ (0.2 ml) and stirred at 47° C. for 7 hrs. Sat.aq. sodium bicarbonate (3 drops) was added and the product was extracted with petrol/ethyl acetate (3×15 ml, 1:1). The combined organic layers were dried and evaporated. Chromatography eluting with 10:1 petrol/ethyl acetate gave (R)-2-{(R)-1-(tert-butyl-dimethylsilyloxy)-16-[(1R,2S)-2-((19S,20S)-19-hydroxy-20-methyloctatriacontyl)-cyclopropyl]hexa-decyl}hexacosanoic acid as a white semi-solid (60 mg, 0.044 mmol, 60%), $[\alpha]_D^{25}$-2.06 (c 0.68, $CHCl_3$).

This compound was treated with PCC in dichloromethane at room temperature for 2 hrs. After work up and chromatography (R)-2-{(R)-1-(tert-butyldimethylsilanyloxy)-16-[(1R,2S)-2-((S)-20-methyl-19-oxo-octatriacontyl)cyclopropyl]hexa-decyl}hexacosanoic acid was obtained as a white semi-solid in 74% yield.

The final TBDMS deprotection was effected by treatment with hydrogen fluoride and pyridine in THF. Chromatography gave a white solid, (R)-2-{(R)-1-hydroxy-16-[(1R,2S)-2-((S)-20-methyl-19-oxo-octatriacontyl)cyclopropyl]hexadecyl}hexacosanoic acid in 83% yield. $[\alpha]_D^{26}$+7.34 (c=0.79, $CHCl_3$), m.p. 66-68° C. {Found (M+Na)$^+$: 1260.2522, $C_{84}H_{164}NaO_4$ requires: 1260.2568}. This showed; $\delta_H$: 3.72 (1H, br., pent, J 4.7 Hz), 2.52 (1H, q, J 6.6 Hz), 2.48 (1H, m), 2.42 (2H, dt, J 1.85, 7.25 Hz), 1.78-1.70 (1H, m), 1.67-1.60 (2H, m), 1.59-1.46 (6H, m), 1.4-1.10 (137H, m), 1.05 (3H, d, J=6.95 Hz), 0.89 (6H, t, J=7.25 Hz), 0.71-0.62 (2H, m), 0.56 (1H, br. dt, J 4.1, 8.5 Hz), −0.33 (1H, br. q, J=5.00 Hz); $\delta_C$: 215.42, 179.80, 72.12, 50.86, 46.33, 41.15, 35.51, 33.04, 31.92, 30.23, 29.71, 29.66, 29.52, 29.50, 29.47, 29.43, 29.37, 29.33, 28.73, 27.33, 25.73, 23.73, 22.69, 16.35, 15.78, 14.11, 10.91, $v_{max}$: 3284, 2919, 2850, 1708, 1465, 1377, 721 cm$^{-1}$.

Example 4

Other Synthetic Mycolic Acids Prepared as Single Compounds

Stereochemically defined synthetic mycolic acid molecules were prepared by analogous methods to that described in relation to example 3 and by methods described in the inventor's previously published papers, the details of which are given above.

Some of the synthetic compounds prepared are shown in table 1:

| Compound number | Structure: |
|---|---|
| 1 | $CH_3(CH_2)_{20}$ with OH, COOH, and $(CH_2)_{19}CH_3$ branches |
| 2 | $CH_3(CH_2)_{19}$ — cyclopropyl — $(CH_2)_{14}$ — cyclopropyl — $(CH_2)_{11}$ — CH(OH)—CH(COOH)($(CH_2)_{23}CH_3$) |
| 3 | $CH_3(CH_2)_{19}$ — cyclopropyl — $(CH_2)_{14}$ — cyclopropyl — $(CH_2)_{11}$ — CH(OH)—CH(COOH)($(CH_2)CH_3$) |
| 4 | $CH_3(CH_2)_{17}$—C(O)—CH(Me)—$(CH_2)_{17}$—CH(Me)—cyclopropyl—$(CH_2)_{15}$—CH(OH)—CH(COOH)($(CH_2)_{23}CH_3$) |

-continued
| Compound number | Structure: |
|---|---|
| 5 | 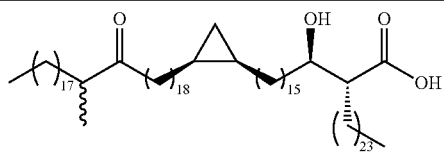 |
| 6 | 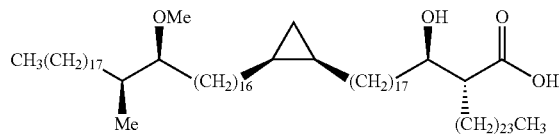 |
| 7 |  |
| 8 | 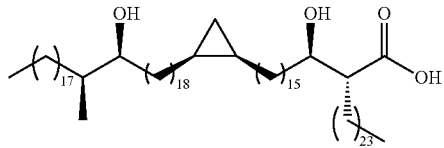 |
| 9 | 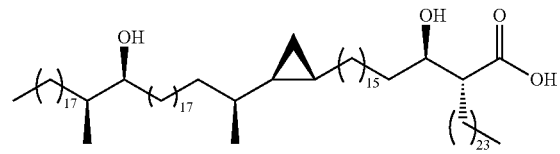 |
| 10 | 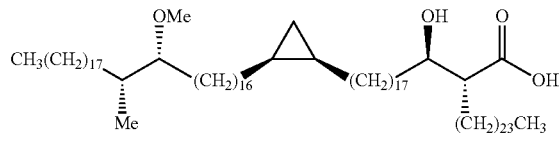 |
| 11 | 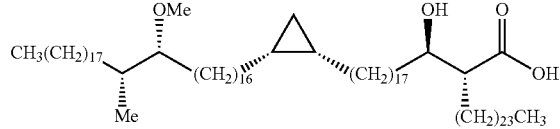 |
| 12 | 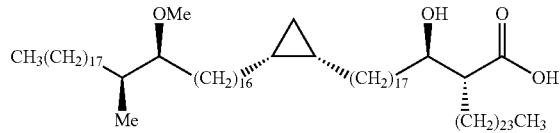 |
| 13 | 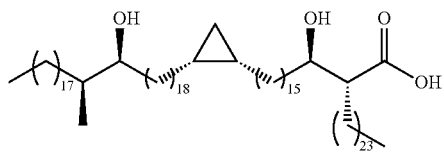 |
| 14 | 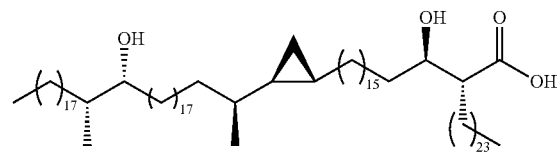 |

-continued

| Compound number | Structure: |
|---|---|
| 15 | |
| 16 | |
| 17 | |
| 18 | |
| 19 | |
| 20 | |
| 21 | |
| 22 | |
| 23 | |
| 24 | |

| Compound number | Structure: |
|---|---|
| 25 | CH₃(CH₂)₁₅—[epoxide]—(CH₂)₁₂—CH=CH—CH(CH₃)—(CH₂)₁₉—CH(OH)—CH((CH₂)₂₁CH₃)—C(=O)OH |

Example 5

Preparation of Mycolic Acid Containing Liposomes and In Vivo Administration

Each of the compounds 1 to 9 listed in table 1 and the natural mycolic acid mixture obtained from sigma (hereinafter crude-MA) were incorporated into liposomes using the method described in Korf J, Stoltz A, Verschoor J, De Baetselier P and Grooten J., Eur J Immunol 2005; 35:890-900. Briefly, the compounds were mixed with phosphatidylcholine (Sigma) in chloroform. The chloroform was evaporated and the lipids recovered in sterile saline. After ultrasound sonication and vortexing, samples of 25 μg mycolic acids/100 μl/mouse were administered intratracheally. A liposome control was prepared similarly, but without the addition of any mycolic acid compound.

Example 6

Assessment of Inflammatory Cell Infiltration to the Airways and Lung Tissue Damage In order to be considered safe for human administration, compounds should preferably cause as little local inflammation or resulting tissue changes as possible.

Inflammatory effects were examined by intratracheally administering to C57BL/6 mice empty liposomes, liposomes carrying the comparative natural sample crude-MA and liposomes carrying the synthetic mycolic acid molecules 3, 4 or 9.

Figure 3:
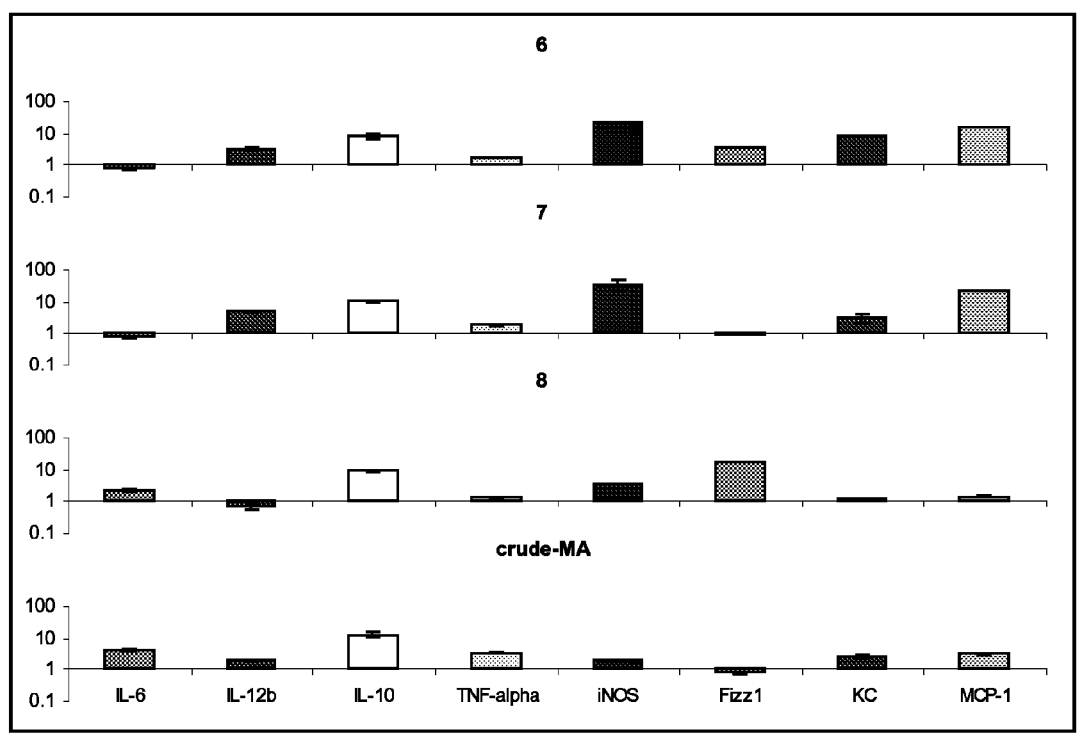

After 48 hours, mice were sacrificed and a broncho-alveolar lavage (BAL) was performed to measure the airway cell types and numbers by flowcytometry. Increased cell numbers and the appearance of granulocytes (mainly neutrophils) in the BAL-fluid are indicative for cell recruitment to the airways as result of an inflammatory reaction. The total cell and neutrophil count of the BAL-fluid is shown in FIG. 3.

Figure 4:
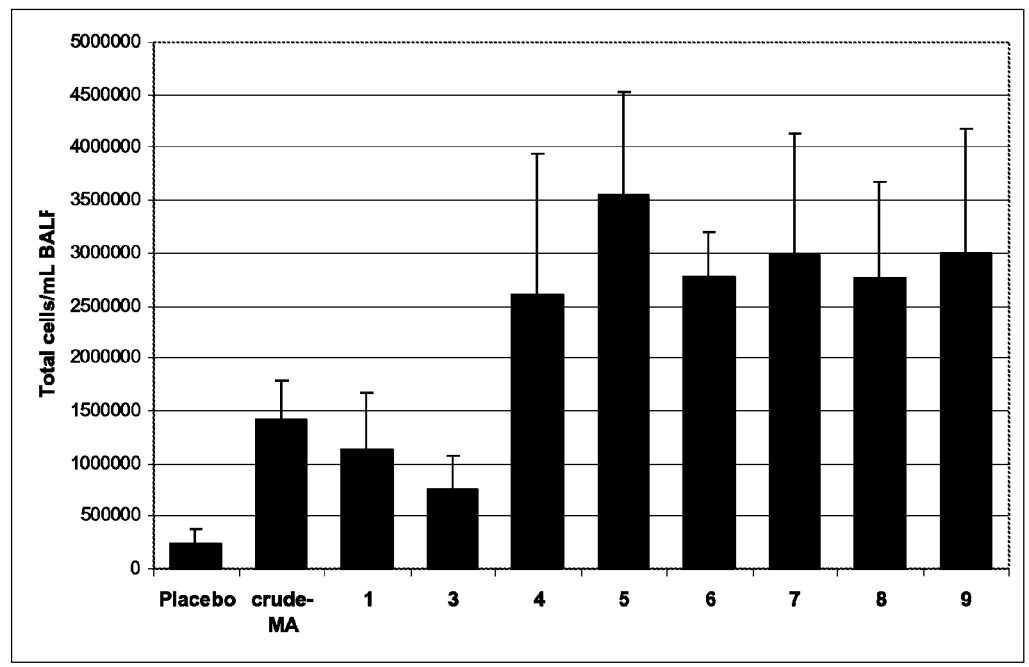

Lavaged lungs were ectomised to allow for histo-pathological examination of the lung tissue. A haematoxylin and eosin staining of the paraffin lung sections was followed by a thorough examination by a skilled pathologist who scored the sections according to the following criteria in a double-blinded manner:
0=no inflammation
1=a minority of the bronchi are surrounded by some infiltrated inflammatory cells
2=the majority of the bronchi are surrounded by some infiltrated inflammatory cells
3=dispersed are some heavy infiltrates of neutrophils and eosinophils
4=a lot of infiltrating neutrophils and eosinophils throughout the entire lung section
5=same as 4 with additionally signs of airway remodelling e.g. basal membrane thickening, mucus overproduction and/or smooth muscle cell hyperplasia The results are shown in FIG. 4 and show that compounds 3, 4 and 9 did not cause any significant lung tissue changes in contrast to the crude-MA comparative sample. These results suggest that use of the synthetic mycolic acid compounds 3, 4 and 9 is safe as the vulnerable mouse lungs are not reacting with inflammation. This lack of reactogenicity is of additive value for use of synthetic mycolic acids in vaccines because there will be little or no discomfort to the patient.

Example 6

Gene Transcription Profiling of Airway CD11c⁺ Cells

Airway CD11c⁺ cells include alveolar macrophages and dendritic cells, which are professional phagocytes and the most important cell types in the early recognition of non-self threats to the airways. Next to mounting an immediate appropriate innate immune response to these threats, CD11c⁺ cells alert and instruct adaptive immune responses by means of 3 different signals: antigen-presentation, surface expression of T-cell co-stimulatory molecules and secretion of instruction cytokines. Whereas dendritic cells migrate to the draining lymph nodes in order to initiate a peripheral antigen-specific immune response, alveolar macrophages remain in the airways to further control local inflammation, but also to locally attract and orchestrate the acquired immune response by lymphocytes.

In order for a locally applied vaccine to be effective, safe adjuvants that give the appropriate signal to CD11c⁺ cells are needed to both increase the immunogenicity of the vaccine and direct the type of the acquired immune response. In order to investigate this for the synthetic mycolic acids of the present invention, mice were treated by intratracheal administration with liposomes comprising compound 6, liposomes comprising compound 7, liposomes comprising compound 8, liposomes comprising the natural mycolic acid mixture, crude-MA and empty liposomes. After 48 hours, the mice were sacrificed and broncho-alveolar lavage performed to measure the CD11c⁺-cell gene transcription by RT-qPCR. The results are shown in FIG. 3 and provide an overview of fold changes in mRNA transcripts for compounds 6, 7, 8 and crude-MA compared to the empty liposome treated control for cytokines (IL-6, IL-12p40, IL-10 and TNF-alpha), macrophage activation markers (iNOS and Fizz1) and chemokines (KC and MCP-1).

IL12p40-containing interleukins IL12 and IL-23 are inflammatory cytokines that, when produced by dendritic cells in the draining lymph nodes, help to mount a strong cellular immune response by directing T-helper (Th) lymphocyte differentiation to interferon-gamma producing Th1 and to Th17 respectively. IL-6 also has a lymphocyte stimulating effect, but local expression by macrophages augments the TNF-alpha-mediated tissue-malign inflammatory response (swelling, redness, pain). IL-10 is an important anti-inflammatory cytokine that locally inhibits TNF-alpha mediated inflammation and directs Th-lymphocyte differentiation by dendritic cells to Th2, important for stimulating B-cells to mount a strong humoral (antibody) response.

As can be seen in FIG. 3, the commercial comparative sample crude-MA was able to induce transcription for all of these cytokines in broncho-alveolar CD11c$^+$ cells, which means that it is potentially a good adjuvant raising both cellular and humoral immune responses. However this mixture might cause too much local macrophage-mediated inflammation (see also example 5). Opposed to this, expression of the inflammatory cytokines TNF-alpha and IL-6 after treatment with synthetic mycolic acids 6, 7 or 8, was less pronounced or absent, whereas induction of expression of the anti-inflammatory and humoral immune response instructing cytokine IL-10 was maintained. Further it is likely that for compounds 6 and 7 the ability to also initiate and orchestrate a cellular adaptive immune response remains as they strongly stimulate the expression of IL-12p40.

Inducible nitric oxide synthetase (iNOS) and Fizz1 are markers for the classical and alternative type of macrophage activation, respectively. It can be seen in FIG. 3 that crude-MA conditioned alveolar macrophages are classically activated, that this type of activation is even more pronounced with compound 7 treatment and that compounds 6 and 8 elicit a mixed type of activation as both iNOS and Fizz1 expression is up regulated. This means that by chemical structure variations of synthetic mycolic acids, the type of macrophage activation can be manipulated in a way desirable for locally directing acquired immune responses.

KC (also CXCL1) and MCP-1 (also CCL2) are both chemokines, produced by alveolar macrophages in order to attract other immune cells to the airways. KC binds to CXCR2 and therefore has chemoattractant activity on neutrophils. MCP-1 attracts CCR2-expressing cells such as monocytes and lymphocytes. From FIG. 3 it can be seen that expression of these chemokines is not induced by molecule 8. This is consistent with the alternative anti-inflammatory expression pattern, and means that the immune response will not be enhanced by additional attraction of immune cells to the site of antigen delivery in a vaccination case (low MCP-1), but also that there is not likely to be any unwanted inflammatory side-effects either (low KC). Compounds 6 and 7 do enhance MCP-1 expression even to a greater extend than crude-MA, but also probably stimulate neutrophil recruitment by means of increased CD11c$^+$ KC-expression. The inflammatory side-effects of these molecules may also be minimal because of a lack of a solid neutrophil-degranulating TNF-alpha response, as mentioned above.

Example 7

Cellular and Humoral Immune Response to Airway Antigen Exposure after Vaccination with the Experimental Antigen Ovalbumin Adjuvanted with Mycolic Acid Liposomes Mice were immunised two times for ovalbumin (OVA) in mycolic acid containing liposomes by intratracheal administration. This was done to verify the adjuvant effect of mycolic acids in vaccine formulations. The intratracheal route was chosen because it is non-invasive and generally difficult to get a good immunisation. This administration route would therefore be of additive value over existing adjuvants. After the immunisation period, mice were exposed three times on consecutive days to aerosolised ovalbumin and the resulting secondary, antigen-induced lung inflammation as well as the systemic serum-antibody response was analysed.

FIG. 4 shows that use of the synthetic mycolic acids 1, 3-9 and the crude-MA comparative sample as adjuvant all resulted in cellular infiltration in response to antigen-challenge, which can be deducted from the increased total cell numbers as compared to a placebo OVA-immunised group. In particular synthetic compounds 4-9 were found to be suited as adjuvants to mount a cellular response upon antigen challenge and outperformed the commercial comparative sample.

Figure 5:
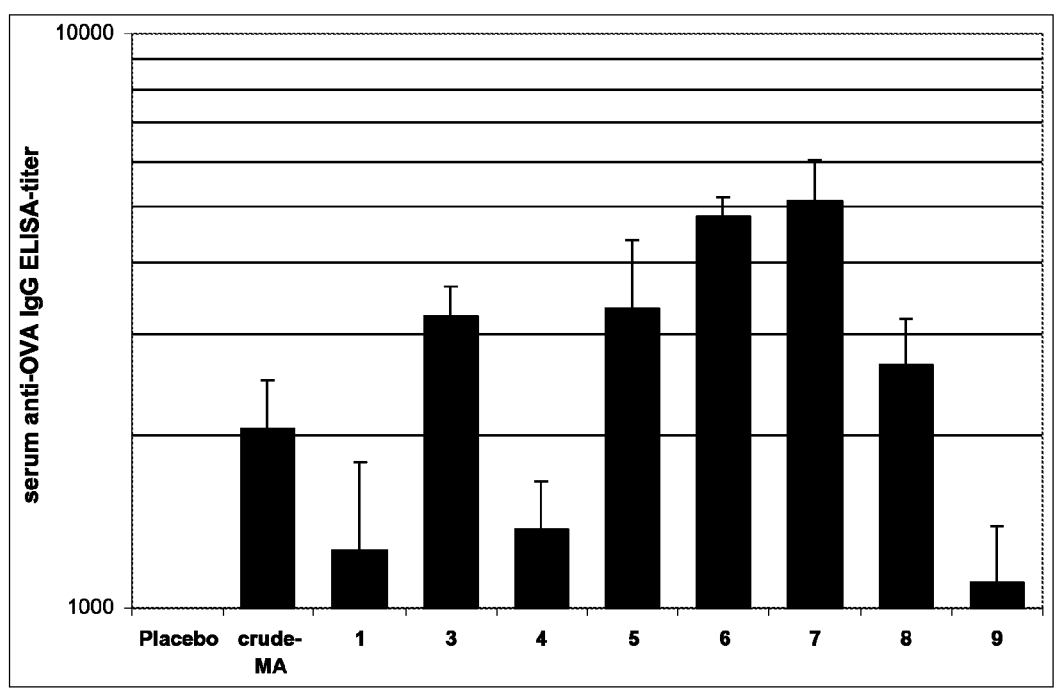

Serum anti-OVA IgG antibody responses were detected for immunisation strategies as above with mycolic acids (crude-MA comparative samples and synthetic 1, 3-9 mycolic acids) containing liposomes, but not after placebo adjuvanted OVA-immunisation, as illustrated in FIG. 5. Although airway challenge with the experimental antigen resulted in only a moderate cellular response after immunisation with compound 3, the serum anti-OVA IgG antibody response is higher (twofold) than with the comparative crude-MA sample. The opposite is true for molecules 4 and 9 as adjuvant. This indicates that different synthetic mycolic acids may be used to direct the type of immune response that is needed for the vaccine application. Compounds 5-8 all elicited strong both cellular and humoral responses against the airway applied experimental vaccine antigen.

Example 8

Vaccine Preparation

A vaccine composition may be prepared comprising a synthetic mycolic acid and inactivated Ag85A from *Mycobacterium tuberculosis* bacteria in a liposome carrier. Ag85A is part of the Ag85 mycolyl-transferase complex and has been shown to have protective potential in experimental *M. tuberculosis* challenge models (McShane H, Pathan A A, Sander C, Keating S M, Gilbert S C, Huygen K, Fletcher H A & Hill A V S. *Nature Med* (10), 1240-1244, 2004). This material may be dispersed in a phosphate buffered saline solution and injected into the muscle of a subject to provide immunity against tuberculosis.

The invention claimed is:
1. A method of administering a vaccine composition to a patient comprising the step of:
administering to the patient a vaccine composition comprising as an adjuvant a compound of formula I:

$$R^1—Z—R^2—Y—R^3—X—R^4\underset{OH}{\overset{R\quad COOP}{<}}\quad (I)$$

as an adjuvant in vaccination;
wherein R is an optionally-substituted alkyl, alkenyl, alkynyl, aryl, arylalkyl or alkylaryl moiety having from 1 to 50 carbon atoms; R$^1$ is an optionally-substituted alkyl, alkenyl, alkynyl, aryl, arylalkyl or alkylaryl moiety having from 1 to 40 carbon atoms; each of R$^2$, R$^3$ and R$^4$ is independently selected from an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkynylene, arylene, alkylarylene or cycloalkylene, ketone, ester, amide, imide, imine, thioether, ether, thioester, thioketone; and P is selected from hydrogen, an alkyl group, or a metal, phosphonium or ammonium species; wherein at least one of X, Y or Z includes a moiety selected from cyclopropyl, C=A, C-AH and C—$OR^5$; wherein $R^5$ is alkyl or haloalkyl, and A is S, O or $NR^6$, wherein $R^6$ may be H or alkyl.

2. A method according to claim 1, wherein in the compound of formula I at least one of X, Y or Z includes a moiety selected from C—$OR^5$ and C=O.

3. A method according to claim 1, wherein in the compound of formula I P is hydrogen.

4. A method according to claim 1, wherein in the compound of formula I each of X, Y and Z is independently selected from one or more of the following units:

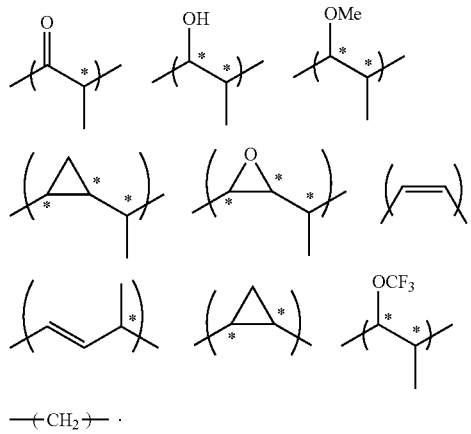

5. A method according to claim 1, wherein in the compound according to claim 1, wherein Y is $CH_2$, X includes a cyclopropyl unit and Z includes a moiety selected from cyclopropyl, C=A, C-AH and C—$OR^5$.

6. A method according to claim 1, wherein in the compound according to claim 1, Z includes a methoxy moiety.

7. A method according to claim 1, wherein the compound according to claim 1 is a compound according to formula IIa, IIb, IIc or IId:

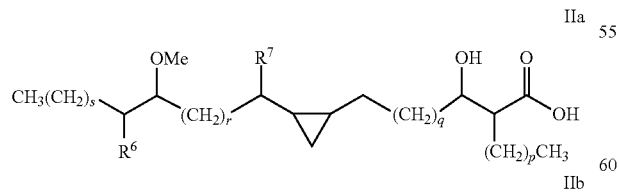

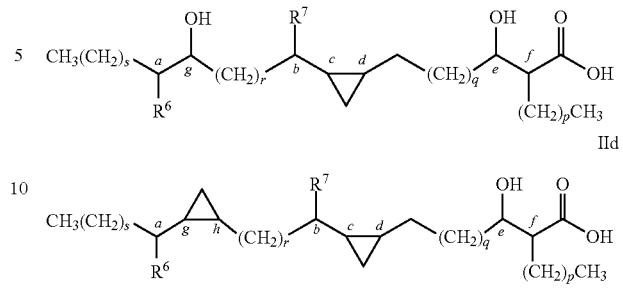

wherein:

$R^6$ is hydrogen or $C_1$ to $C_4$ alkyl, $R^7$ is hydrogen or $C_1$ to $C_4$ alkyl, p has a value of from 16 to 30, q has a value of from 8 to 24, r has a value of from 12 to 28 and s has a value of from 12 to 28.

8. A method according to claim 1, wherein in the compound of formula I is a synthetically prepared compound.

9. A method of administering a vaccine composition to a patient comprising the step of:

administering to the patient a vaccine composition comprising as an adjuvant a compound of formula I:

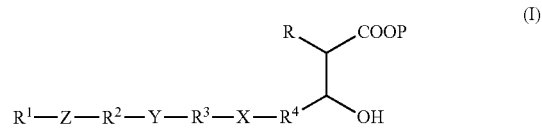

as an adjuvant in vaccination;

wherein R is an optionally-substituted alkyl, alkenyl, alkynyl, aryl, arylalkyl or alkylaryl moiety having from 1 to 50 carbon atoms; $R^1$ is an optionally-substituted alkyl, alkenyl, alkynyl, aryl, arylalkyl or alkylaryl moiety having from 1 to 40 carbon atoms; each of $R^2$, $R^3$ and $R^4$ is independently selected from an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkynylene, arylene, alkylarylene or cycloalkylene, ketone, ester, amide, imide, imine, thioether, ether, thioester, thioketone; and P is selected from hydrogen, an alkyl group, a, or a metal, phosphonium or ammonium species; wherein at least one of X, Y or Z includes a moiety selected from cyclopropyl, C=A, C-AH and C—$OR^5$; wherein $R^5$ is alkyl or haloalkyl, and A is S, O or $NR^6$, wherein $R^6$ may be H or alkyl except for compounds of one or more of the following formula:

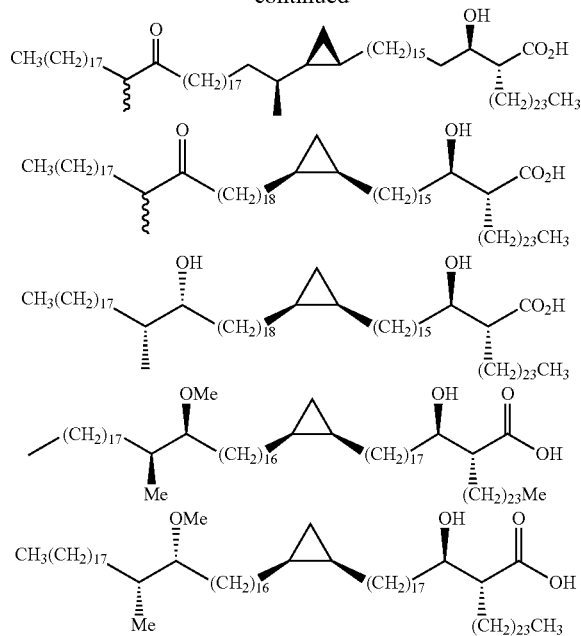

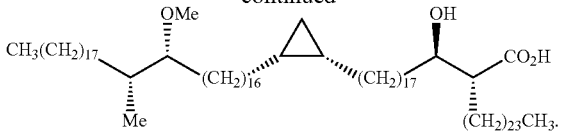

10. A method according to claim 1, wherein the vaccine composition further comprises an antigen.

11. A method according to claim 10 in which the vaccine composition further comprises a pharmaceutically acceptable carrier.

12. A method according to claim 11 in which the pharmaceutically acceptable carrier comprises a liposome.

13. A method of raising cellular immune responses where the level of immune protection raised will benefit from a cellular immune defence component, the method comprising the step of; administering a vaccine composition which comprises a compound according to formula I of claim 1 as an adjuvant.

14. A method of raising cellular immune responses comprising the step of:
    administering to a patient a vaccine composition comprising a compound of formula I according to claim 1.

* * * * *